US012778503B2

(12) United States Patent
Nikishov et al.

(10) Patent No.: US 12,778,503 B2
(45) Date of Patent: Nov. 3, 2026

(54) METHOD AND SYSTEM FOR ESTIMATION OF ABDOMINAL FAT

(71) Applicant: Samsung Electronics Co., Ltd., Suwon-si (KR)

(72) Inventors: Artem Yurievich Nikishov, Kolomna (RU); Jonghee Han, Suwon-si (KR); Minhyoung Lee, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 19/062,890

(22) Filed: Feb. 25, 2025

(65) Prior Publication Data

US 2025/0185991 A1 Jun. 12, 2025

Related U.S. Application Data

(63) Continuation of application No. PCT/KR2023/011552, filed on Aug. 7, 2023.

(30) Foreign Application Priority Data

Aug. 27, 2022 (RU) ........................... RU2022123010

(51) Int. Cl.

*A61B 5/00* (2006.01)
*A61B 5/0537* (2021.01)
*G16H 50/30* (2018.01)

(52) U.S. Cl.

CPC .......... *A61B 5/4872* (2013.01); *A61B 5/0537* (2013.01); *A61B 5/681* (2013.01); (Continued)

(58) Field of Classification Search

CPC ... A61B 5/0507; A61B 5/4872; A61B 5/0537; A61B 5/681; A61B 5/6898; A61B 5/7267; G16H 50/30; G01S 13/867

See application file for complete search history.

(56) References Cited

U.S. PATENT DOCUMENTS 7,813,794 B2 10/2010 Oku et al.
RE42,833 E 10/2011 Serita et al.
(Continued)

FOREIGN PATENT DOCUMENTS

CN 111887847 A 11/2020
CN 112419479 A 2/2021
(Continued)

OTHER PUBLICATIONS

Extended European Search Report dated Nov. 14, 2025 issued in European Patent Application No. 23860718.8.
(Continued)

*Primary Examiner* — Gerald Johnson
(74) *Attorney, Agent, or Firm* — NIXON & VANDERHYE P.C.

(57) ABSTRACT

The disclosure relates to studying physical properties of biological tissues, and for example, to a method and system for indirect estimation of the abdominal subcutaneous fat area and the abdominal visceral fat area. The technical result is reduced complexity and increased accuracy and speed of estimation of the abdominal subcutaneous fat area and the abdominal visceral fat area with portable devices. A method for determining the abdominal visceral fat area and the subcutaneous fat area in a body section in an abdominal region, comprises: using a device with ultra-wide band (UWB) radar applied to the body in the abdominal region, emitting radiation into the body and measuring parameters of reflected radiation; based on the reflected radiation measurement data obtained by the UWB radar, determining the abdominal subcutaneous fat area (ASFA) in the body section, corresponding to the measurement point; acquiring anthropometric data and bio-electrical impedance value of the body; based on the bio-electrical impedance data of the body and the anthropometric data, determining total fat area (Continued)

(TFA) in the body section in the abdominal region; calculating the abdominal visceral fat area (AVFA) in the body section from the determined total fat area and the abdominal subcutaneous fat area.

14 Claims, 6 Drawing Sheets

(52) U.S. Cl.
CPC .......... *A61B 5/6898* (2013.01); *A61B 5/7267* (2013.01); *G16H 50/30* (2018.01)

(56) References Cited

U.S. PATENT DOCUMENTS

| | | | | |
|---|---|---|---|---|
| 10,765,362 | B2 | 9/2020 | Ajima | |
| 11,082,503 | B2 | 8/2021 | Aoki | |
| 11,376,634 | B2 | 7/2022 | Nagafuchi et al. | |
| 11,412,947 | B2 | 8/2022 | Jung et al. | |
| 2006/0282005 | A1 | 12/2006 | Kasahara et al. | |
| 2009/0018463 | A1 | 1/2009 | Tamura et al. | |
| 2009/0093732 | A1* | 4/2009 | Kasahara | A61B 5/4872 600/547 |
| 2013/0281820 | A1* | 10/2013 | Payne | A61B 5/4872 600/407 |
| 2014/0121564 | A1* | 5/2014 | Raskin | A61B 5/0022 600/587 |
| 2016/0143558 | A1 | 5/2016 | Chernokalov et al. | |
| 2016/0249857 | A1* | 9/2016 | Choi | A61B 5/4872 600/547 |
| 2019/0104992 | A1 | 4/2019 | Magar et al. | |
| 2020/0367816 | A1* | 11/2020 | Panneer Selvam | A61B 5/7475 |
| 2022/0117509 | A1* | 4/2022 | Garff | G16H 50/30 |
| 2023/0065288 | A1* | 3/2023 | Valsan | A61B 5/4872 |
| 2024/0395408 | A1* | 11/2024 | Li | G16H 50/20 |

FOREIGN PATENT DOCUMENTS

| | | | | |
|---|---|---|---|---|
| EP | 1464280 | A2 | 10/2004 | |
| EP | 3501399 | A1 | 6/2019 | |
| EP | 3505050 | A1 * | 7/2019 | A61B 5/4869 |
| KR | 101821317 | B1 | 1/2018 | |
| KR | 20200124957 | A | 11/2020 | |
| RU | 2578298 | C1 | 3/2016 | |
| RU | 2694026 | C1 | 7/2019 | |
| RU | 2739726 | C1 | 12/2020 | |

OTHER PUBLICATIONS

Elmissaoui et al., Optimization of the UWB Radar System in Medical Imaging, Journal of Signal and Information Processing, vol. 2, No. 3, pp. 227-231, 2011.
International Search Report and Written Opinion of the ISA for PCT/KR2023/011552 mailed Nov. 14, 2023, 9 pages.
RU Search Report for 2022123010 dated Jan. 10, 2023, 2 pages.
RU Decision on Grant for 2022123010 dated Jun. 1, 2023, 11 pages.
RU Office Action for 2022123010 dated Jan. 27, 2023, 12 pages.

* cited by examiner

METHOD AND SYSTEM FOR ESTIMATION OF ABDOMINAL FAT

CROSS-REFERENCE TO RELATED APPLICATIONS

This application is a continuation of International Application No. PCT/KR2023/011552 designating the United States, filed on Aug. 7, 2024, in the Korean Intellectual Property Receiving Office and claiming priority to Russian Patent Application No. 2022123010, filed on Aug. 27, 2022, in the Russian Patent Office, the disclosures of each of which are incorporated by reference herein in their entireties.

BACKGROUND

Field

The disclosure relates to studying physical properties of biological tissues, and for example, to a method and system for indirect estimation of the abdominal subcutaneous fat area (ASFA) and the abdominal visceral fat area (AVFA).

Description of Related Art

ASFA and AVFA values can be used to estimate a person's health status, make recommendations for nutrition and treatment adjustments, etc. Such data can be especially useful for athletes or people who most need to control their body composition, for example, those who have suffered injuries or are obese. ASFA and AVFA can be estimated based on the abdominal subcutaneous fat thickness, gender, age of the user, anthropometric data (waist, height, weight, etc.), total body fat mass and/or body impedance value (upper value, lower value, general value).

High accuracy (error of about 5 cm2) estimation of ASFA and AVFA is possible via professional medical equipment such as magnetic resonance imaging (MRI) or computer-assisted tomography (CT) devices. However, this method exhibits high cost and long time of examination. In addition, most users have no opportunity to frequently conduct such studies due to lack of access to professional medical equipment.

Therefore, the task of implementing ASFA and AVFA estimation with low-cost portable devices (for example, smartphones and smart watches) is relevant for many users.

Currently, the use of ultra-wideband (UWB) radars, for example, impulse-radio (IR) ultra-wideband radars (IR UWB), in smartphones for the purposes of biometric research is seen as promising. Furthermore, in professional medicine, bio-electrical impedance analysis (BIA) has been known for a relatively long time and is used to measure body composition as a non-invasive method enabling short time analysis of body composition: determining the amount of fluid, fat mass and muscles, bone tissue, body mass index, metabolic rate, biological age, predisposition to certain diseases, etc. At the same time, in recent years, there has been an active growth in embedding the bio-electrical impedance analysis methods into small wearable devices, such as smart watches and fitness bracelets, which is extremely attractive for a wide range of users who care about their health, work on fitness, strive to lose weight, etc.

FIG. 1 is a diagram illustrating an approximate human body structure with highlighted areas corresponding to subcutaneous fat, muscles and visceral fat, and also schematically shows layers corresponding to the highlighted areas. FIG. 1 depicts an example human body structure to illustrate known problems that occur when measuring subcutaneous and visceral fat area with UWB radar.

FIG. 1, in a right side, an example image 10 of a human body section in the abdominal region is shown, obtained e.g. by magnetic resonance imaging, with highlighted regions corresponding to subcutaneous fat, muscles and visceral fat, and in a left side, layers 20 corresponding to the highlighted regions is schematically shown.

In this context, "human body section" is understood as an image obtained by mentally dissecting the human body with a plane perpendicular to the longitudinal axis of the human body.

In the process of examining a human body with UWB radar applied to the human skin 21, the UWB radar emits radiation into the body and receives reflected radiation. Since permittivity (dielectric constant) of muscles 23 ($\varepsilon$=44.1) is about 10 times higher than that of subcutaneous fat 22 ($\varepsilon$=4.7), most of the electromagnetic signal emitted by the radar is reflected from the muscle layer. Although part of the emitted electromagnetic signal still penetrates the muscles 23, most of this signal will be re-reflected in the muscles 23 acting as a resonator. Even if part of the emitted electromagnetic signal penetrates the visceral fat 24 and is reflected by visceral organs 25, most of this signal will be attenuated by the processes described above. Thus, at the moment, it is not possible to estimate and differentiate ASFA and AVFA only using UWB radar with a safe power level of electromagnetic radiation.

US 2016/0143558 A1 discloses an electronic device, including a receiver configured to receive signals reflected from an object; and a controller configured to generate information corresponding to at least one tissue layer of the object based on the signals and a plurality of positions of the electronic device, wherein the plurality of positions are determined while the electronic device moves.

However, safe dose of electromagnetic radiation does not allow measuring internal abdominal visceral fat value with the IR UWB radar of SISO (Single In and Single Out) type disclosed in the document due to high energy consumption by muscles and visceral organs.

Patent document US RE42833 E discloses a method and an apparatus for measuring a distribution of body fat for human body. The method comprises measuring bioelectrical impedance and thickness of abdominal subcutaneous fat, based on the personal data such as sex, age, height, weight, etc. However, the method is based on the using caliper or ultrasound signal and unsuitable for portable devices, like smartphone and smart watch. In addition, the disclosure does not involve the use of UWB radar.

Patent document KR20200124957A discloses including an IR-UWB radar sensing unit which irradiates an impulse radio signal to an abdomen, receives the reflected impulse radio signal, and outputs the received impulse radio signal as sensing result information; and a determination result output unit which converts the determination result information into visual information. However, the system uses multi-in and multi-out system (MIMO) which is complex and bulky, thereby limiting the applicability in portable devices.

Patent document U.S. Pat. No. 7,813,794 B2 discloses a body fat measuring apparatus, in which a constant electric-current is flowed between hand electric-current electrodes and leg electric-current electrodes. From two detected voltages generated between an annular-shaped voltage electrode placed on an abdominal portion and two voltage electrodes placed at the both sides of a lumbar portion, two abdominal impedances are determined. Two electric-current electrodes and two voltage electrodes are placed such that they are spaced apart by a small interval from one another at an umbilicus portion. However, the disclosure features complex hardware and uses only bio-electrical impedance calculation, preventing distinguishing ASFA and AVFA.

Thus, there is a need in the art for a method and system for estimation and differentiation of abdominal subcutaneous fat and abdominal visceral fat, which would address at least the following drawbacks of existing proposals:

need to use professional stationary medical equipment;

complexity of implementation;

long examination process;

infeasibility of implementing via portable devices.

The above information is presented as background information simply to assist with an understanding of the disclosure. No determination has been made, and no assertion is made, as to whether any of the above might be applicable as prior art with regard to the disclosure.

SUMMARY

According to an example embodiment a method for determining an abdominal visceral fat area (AVFA) and an abdominal subcutaneous fat area (ASFA) in a body section in the abdominal region, is provided, comprising:

- using a device with ultra-wide band (UWB) radar, emitting radiation into a body in the abdominal region and measuring parameters of reflected radiation;
- based on the measured parameters of the reflected radiation obtained by the UWB radar, determining the ASFA in the body section of the body, corresponding to the measurement point;
- acquiring anthropometric data and bio-electrical impedance data of the body;
- based on the bio-electrical impedance data of the body and the anthropometric data, determining total fat area (TFA) in the body section in the abdominal region; and
- calculating the AVFA in the body section from the determined TFA and the ASFA.

According to an embodiment of the method, the device with UWB radar is applied to the body in the umbilical region.

According to an embodiment of the method, determining the ASFA comprises: comparing the measured parameters of the reflected radiation with specified threshold values, corresponding to a specified thickness of abdominal subcutaneous fat, and based on the comparison, obtaining data on the thickness of the abdominal subcutaneous fat at the measurement point and data on the ASFA in the body section corresponding to the measurement point.

According to an embodiment of the method, the specified threshold values are specified based on a plurality of measurements taken on a reference sample of people, and to match the specified threshold values, the thickness of the abdominal subcutaneous fat and the ASFA are determined by a reference method.

According to an embodiment, the method comprises: determining, for each of the reflected radiation measurement data, which of the specified threshold values the each of the reflected radiation measurement data is closer to, and determining a subcutaneous fat thickness value.

According to an embodiment of the method, based on multiple measurements, the thickness value of the abdominal subcutaneous fat is determined by averaging the obtained thickness value of the abdominal subcutaneous fat based on the measured parameters of the reflected radiation.

According to an embodiment of the method, based on multiple measurements, the thickness value of the abdominal subcutaneous fat is determined by determining the thickness value of the abdominal subcutaneous fat occurring more often than remaining values based on the measured parameters of the reflected radiation, and discarding the remaining.

According to an embodiment of the method, the measured parameters of reflected radiation include amplitude and/or phase of a signal.

According to an embodiment of the method, the measured parameters of the reflected radiation are processed by a neural network trained on a dataset corresponding to the reference sample of people and including values of the thickness of the abdominal subcutaneous fat and ASFA, obtained using a reference method and respective values of the measured parameters of reflected radiation.

According to an embodiment of the method, the bio-electrical impedance data of the body is obtained with a bio-impedance analysis (BIA) device.

According to an embodiment of the method, the bio-electrical impedance data of the body and the anthropometric data are stored in memory and retrieved from memory for further processing.

According to an embodiment of the method, the bio-electrical impedance data of the body and the anthropometric data are input via an interface for further processing.

According to an embodiment of the method, wherein the TFA in the body section in the abdominal region is determined based on the equation:

$$TFA = \alpha \cdot BII + \beta \cdot W + \gamma \cdot G + \delta \cdot E,$$

where, BII is a body impedance index of the body, W is the weight of a subject, G is gender, E is age, α, β, γ, δ are coefficients, wherein:

$$BII = H^2 / Z_{body},$$

where H is height, Zbody is the bio-electrical impedance value.

According to an embodiment of the method, the TFA in the body section in the abdominal region is determined by one of the equations:

$$TFA = \alpha 0 \cdot BII + \beta 0 \cdot W + \delta 0 \cdot E \text{—for female,}$$

$$TFA = \alpha 1 \cdot BII + \beta 1 \cdot W + \delta 1 \cdot E \text{—for male,}$$

where α0, α1, β0, β1, δ0, δ1 are coefficients.

According to an embodiment of the method, coefficients α, β, γ, δ or coefficients α0, α1, β0, β1, δ0, δ1 are determined by a neural network trained on a dataset corresponding to the reference sample of people and including anthropometric data of subjects, bio-electrical impedance data and the TFA in the body section in the abdominal region, determined by the reference method.

According to an embodiment of the method, the AVFA is determined by the equation:

$$AVFA = \vartheta \cdot TFA - \theta \cdot ASFA,$$

where υ and θ are coefficients determined by a neural network trained on a dataset corresponding to a reference sample of people and including the ASFA and the TFA in the abdominal region, obtained from the measured parameters of the reflected radiation, the bio-electrical impedance data and the anthropometric data, and the abdominal visceral fat area, determined by the reference method.

According to an embodiment of the method, the reference method is selected from magnetic resonance imaging and computer-assisted tomography.

In accordance an example embodiment, there is provided a system configured to determine an abdominal subcutaneous fat area (ASFA) and an abdominal visceral fat area (AVFA), comprising:

a device comprising circuitry including embedded ultra wide-band (UWB) radar, configured to emit radiation into a in an abdominal body and measure parameters of reflected radiation;

a bio-electrical impedance analysis device comprising circuitry configured to measure bio-electrical impedance data of a body, and a processing unit including at least one processor, comprising processing circuitry, individually and/or collectively, configured to:

determine the ASFA in a body section of the body based on the measured parameters of the reflected radiation obtained by the UWB radar;

determine total fat area (TFA) in the body section in the abdominal region based on bio-electrical impedance data of the body and anthropometric data, and calculate the AVFA from the obtained TFA and the ASFA.

According to an embodiment of the system, the device including the UWB radar circuitry includes a smartphone with embedded UWB radar, and the bio-electrical impedance analysis device includes a smart watch capable of measuring bio-electrical impedance of the body.

According to an embodiment of the system, the device including the UWB radar circuitry and the bio-electrical impedance analysis device are implemented in a single device, comprising a smartphone.

According to an embodiment of the system, at least one processor resides in a smartphone.

In accordance with an example embodiment, there is provided non-transitory computer-readable medium that stores instructions causing at least one processor, individually and/or collectively, to perform the method of claim 1 when executed.

Embodiments of the disclosure provide a method and system that provides a simple, accurate and fast process for estimating the abdominal subcutaneous fat area (ASFA) and the abdominal visceral fat area (AVFA) using portable devices.

These and other features and advantages of the present disclosure will become more apparent upon reading the following detailed description with reference to the accompanying drawings.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

According to various example embodiments, there is provided a method for determining an abdominal visceral fat area (AVFA) and the abdominal subcutaneous fat area (ASFA) in a body section in the abdominal region (see FIG. 2), comprising:

using a device with ultra-wide band (UWB) radar, emitting radiation into a body in the abdominal region and measuring parameters of reflected radiation (step S1);

based on the measured parameters of the reflected radiation obtained by the UWB radar, determining the abdominal subcutaneous fat area (ASFA) in the body section of the body corresponding to the measurement point (step S2);

acquiring anthropometric data and bio-electrical impedance data of the body (step S3);

based on the bio-electrical impedance data of the body and the anthropometric data, determining total fat area (TFA) in the body section (step S4);

calculating the abdominal visceral fat area in the body section from the determined total fat area and the abdominal subcutaneous fat area (step S5).

Hereinafter, various operations of the above method will be described in greater detail.

Figure 1:
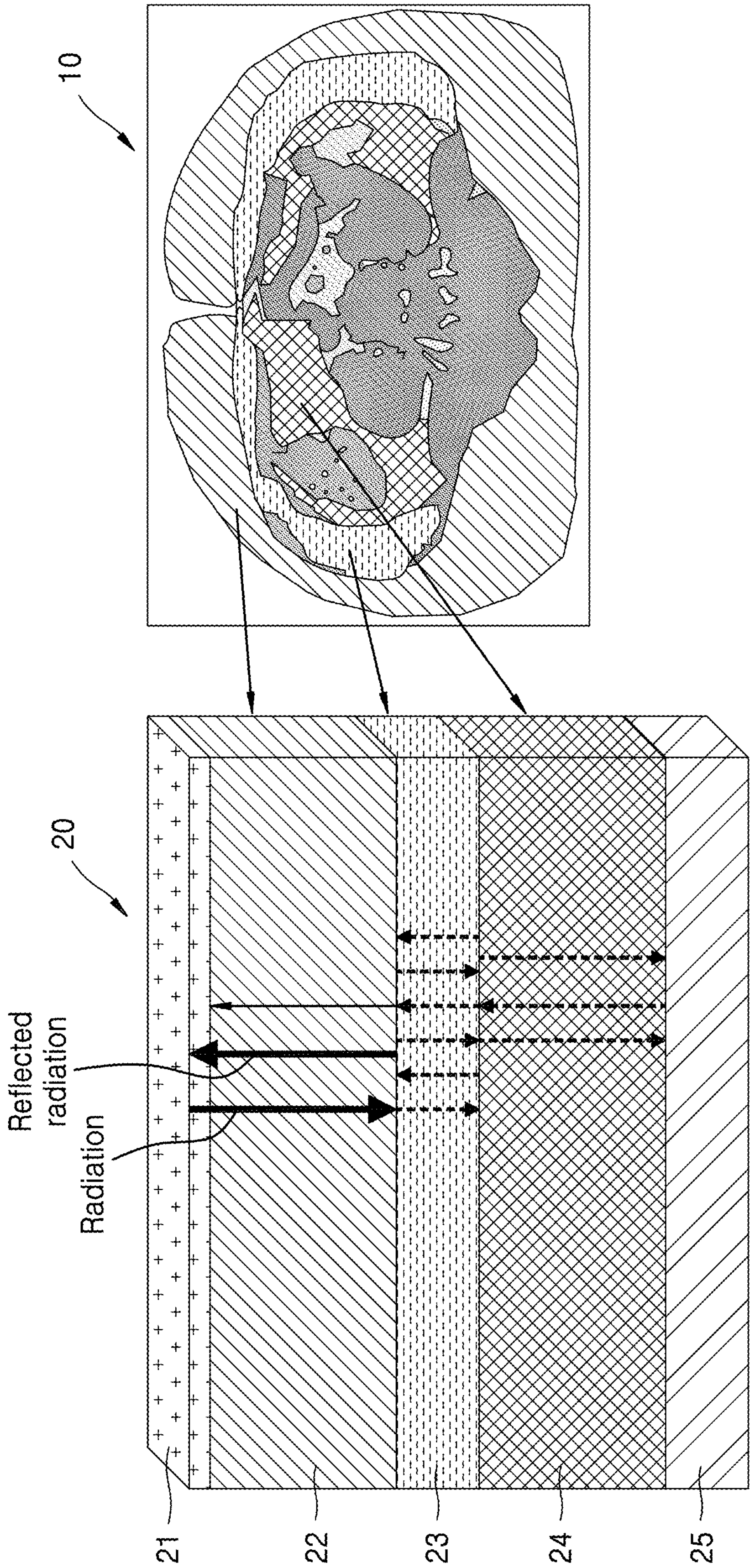
FIG. 1 is a diagram illustrating an approximate human body structure with highlighted areas corresponding to subcutaneous fat, muscles and visceral fat, and also schematically illustrating layers corresponding to the highlighted areas.
Figure 2:
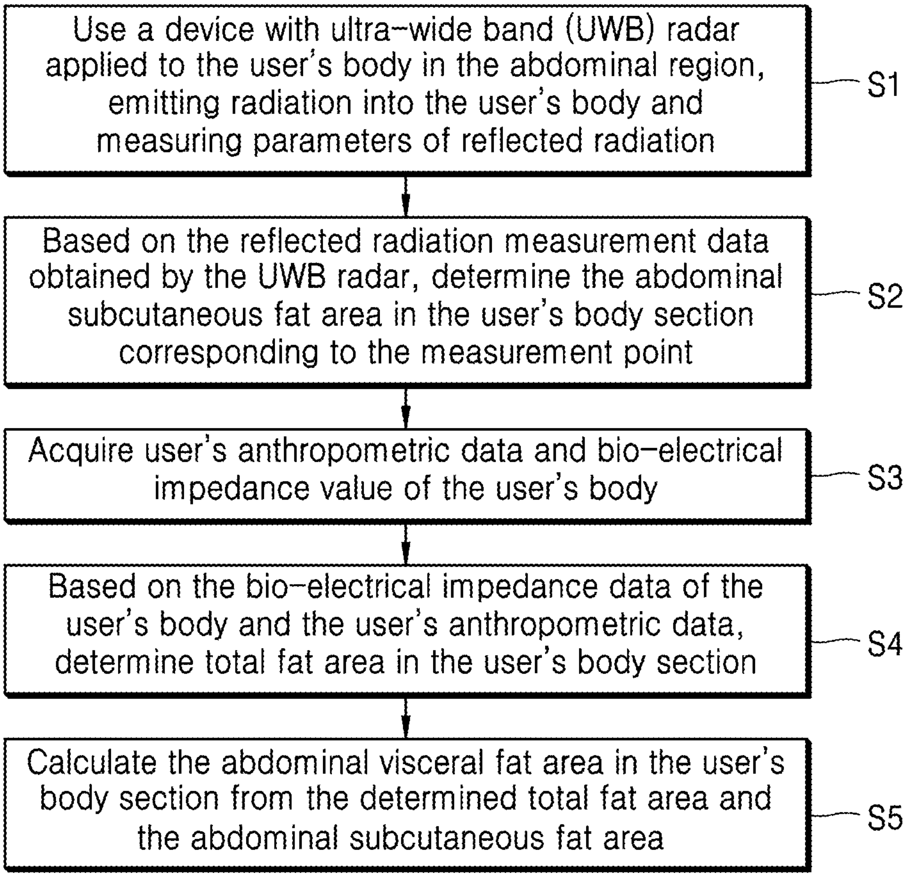
FIG. 2 is a flowchart illustrating an example process for determining the abdominal subcutaneous fat area and abdominal visceral fat area according to various embodiments.

FIG. 2 is a flowchart illustrating an example process for determining the abdominal subcutaneous fat area and abdominal visceral fat area according to various embodiments.

Referring to FIG. 2, at step S1, a device with ultra-wideband radar is applied to a body, e.g., a user's body, in the abdominal region, for example, in the umbilical region (in the range of 3-10 cm from the navel) (mesogaster). The ultra-wideband radar emits electromagnetic radiation into the body and measures parameters (e.g. amplitude, phase) of reflected radiation. The UWB radar can use different operating frequency bands (e.g. high and low frequencies), pulse shapes, signal modulation methods (e.g. unmodulated signal, frequency-modulated signal, etc.) when emitting. Measurements are taken at least once at least at one point. To enhance accuracy of the result, measurement can be taken several times with slightly changing the radar position. In doing this, the UWB radar radiation has safe power level.

At step S2, the obtained raw measurement results in the form of reflected signal (amplitude and phase) with a specified sampling step are compared with predetermined (e.g., specified) thresholds corresponding to a specified thickness of abdominal subcutaneous fat, and based on the comparison, data on the thickness of the abdominal subcutaneous fat at the measurement point and data on the abdominal subcutaneous fat area in the body section corresponding to the measurement point are obtained.

The thresholds of reflected signal amplitude and phase for respective thickness and abdominal subcutaneous fat area are determined based on a plurality of measurements performed on a sample of people (the larger the sample, the more accurately this match is established). To match the thresholds of the reflected signal level, the thickness and abdominal subcutaneous fat area are determined using a reference (e.g., gold standard) method which features high accuracy of the results obtained, for example, magnetic resonance imaging or computer-assisted tomography. The reference (e.g., gold standard) method refers to a research method used to obtain data to be used as ground truth in subsequent processing.

Figure 3A:
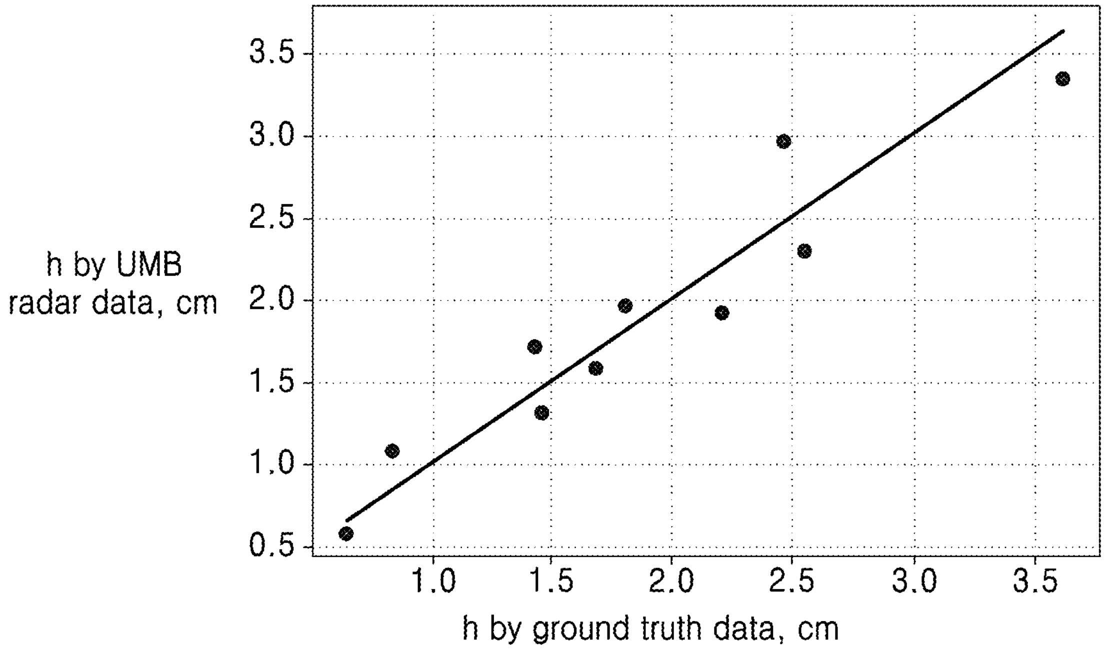
FIG. 3A is a graph illustrating relationships between subcutaneous fat thickness determined by reference method and subcutaneous fat thickness calculated according to various embodiments.
Figure 3B:
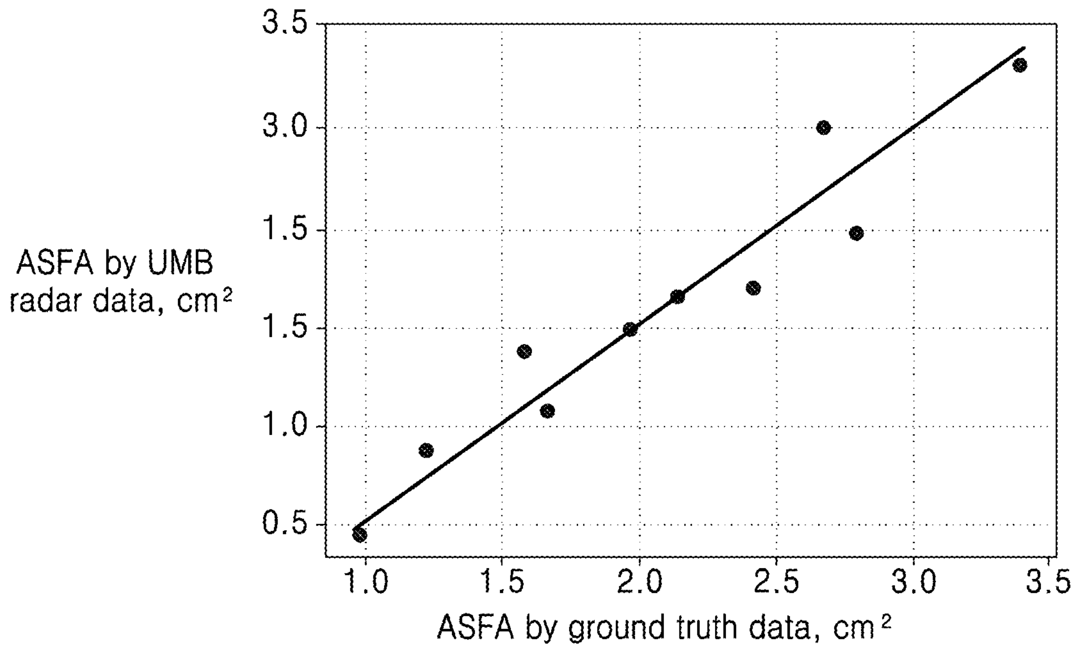
FIG. 3B is a graph illustrating relationships between subcutaneous fat area determined by reference method and subcutaneous fat area calculated according to various embodiments.

Based on the studies carried out, results of measuring the reflected signal have a high coefficient of correlation with the thickness of the abdominal subcutaneous fat at the measurement point in the abdominal region. Furthermore, the thickness of the abdominal subcutaneous fat at the measurement point has a high coefficient of correlation with the abdominal subcutaneous fat area in the abdominal region section corresponding to the measurement point. FIG. 3A and FIG. 3B are graphs illustrating these relationships. FIG. 3A shows relationships between thickness of abdominal subcutaneous fat determined by reference method and thickness of abdominal subcutaneous fat calculated according to various embodiments. FIG. 3B shows relationships between abdominal subcutaneous fat area determined by reference method and abdominal subcutaneous fat area calculated according to various embodiments.

FIG. 3A shows thickness value of the abdominal subcutaneous fat calculated according to various embodiments from reflected signal measurement results (h by UMB radar data) versus thickness value of the abdominal subcutaneous fat determined by reference method (h by ground truth data). FIG. 3B shows abdominal subcutaneous fat area (ASFA) value calculated according to various embodiments from reflected signal measurement results (ASFA by UMB radar data) versus abdominal subcutaneous fat area value determined by reference method (ASFA by ground truth data).

Sampled measurement values of reflected signal parameters at each sampling point are compared with the aforementioned specified thresholds. For each sampled value, it is determined which of the thresholds the each sampled values is closer to, and respective thickness value of the abdominal subcutaneous fat is determined. Final thickness value of the abdominal subcutaneous fat is determined by averaging all obtained thickness value of the abdominal subcutaneous fat for the measurements taken. In an example embodiment, final thickness value of the abdominal subcutaneous fat is determined by determining the most frequently occurring thickness value of the abdominal subcutaneous fat for the measurements taken, and discarding the rest of obtained values.

Referring to FIG. 3A, in an example embodiment, the vertical axis value of a point refers to the calculated thickness value of the abdominal subcutaneous fat and the horizontal axis value of the point refers to the thickness value of the abdominal subcutaneous fat determined according to the ground truth data.

Based on the determined final thickness value of the abdominal subcutaneous fat, a processing unit (e.g., including at least one processor comprising processing circuitry) determines the abdominal subcutaneous fat area (ASFA) in the body section corresponding to the measurement point.

Referring to FIG. 3B, in an example embodiment, the vertical axis value of a point refers to the calculated abdominal subcutaneous fat area and the horizontal axis value of the point refers to the abdominal subcutaneous fat area determined according to the ground truth data.

To reduce the computational load and increase the speed of processing the measurement results, the above processing may not be performed for all sampled values of the measured parameters of the reflected radiation, e.g. part of sampled points can be excluded from processing. For the same purpose, one of measured parameters can be processed, e.g. for example amplitude values or phase values of the reflected radiation can be excluded from processing.

In addition, the measurement results for reflected radiation can be processed in both the time and frequency domain.

Processing of obtained results of measuring the reflected radiation at step S2 for determining the thickness of the abdominal subcutaneous fat and respective abdominal subcutaneous fat area in an embodiment can be performed by a neural network pre-trained on the dataset described above (subcutaneous fat thickness and area values obtained by reference method and respective values of reflected radiation parameters) corresponding to a reference sample of people, using conventional machine learning (ML) methods, e.g. decision tree. Random forest, Gaussian process regression, k-nearest neighbors, etc. can be used. Thus, the neural network is pre-trained on a dataset obtained for a reference sample of people and including the thickness of the abdominal subcutaneous fat and abdominal subcutaneous fat area values obtained by reference method, and respective values of reflected radiation parameters. At step S2, the trained neural network processes the obtained measurement results of the reflected radiation to obtain data on the thickness and area of the abdominal subcutaneous fat in the examined body section corresponding to the measurement point.

At step S3, anthropometric data and bio-electrical impedance value of the body are obtained.

In an example embodiment, bio-electrical impedance of the body at step S3 is measured using a bio-electrical impedance analysis (BIA) device (e.g., including various circuitry).

Information about bio-electrical impedance of the body can include bio-electrical impedance of the upper body (measured between points on user's arms), bio-electrical impedance of the lower body (measured between points on user's legs) or bio-electrical impedance of the entire body. More accurate measurement results are obtained when bio-electrical impedance of the entire body is measured. However, for measuring partial bio-electrical impedance (bio-electrical impedance of the upper body or bio-electrical impedance of the lower body), smaller devices with fewer electrodes can be used.

In an example embodiment, bio-electrical impedance value of the body can be pre-stored in memory, and at step S3 it can be retrieved from memory and transferred to the processing unit. In an example embodiment, bio-electrical impedance value of the user's body may be input at step S3 into the processing unit via input/output (I/O) interface.

For purposes of the disclosure, it is assumed that the total fat area in each body section in the abdominal region is approximately the same. Based on the obtained value of bio-electrical impedance ($Z_{body}$) and the user's anthropometric data, at step S4, total fat area in the abdominal region section may be determined using the equation:

$$TFA = \alpha \cdot BII + \beta \cdot W + \gamma \cdot G + \delta \cdot E, \quad (1)$$

where TFA is the total fat area, BII is the body impedance index of the body, W is the weight, G is the user's gender, E is the age, α, β, γ, δ are coefficients, wherein:

$$BII = H^2 / Z_{body}, \quad (2)$$

where H is the height and $Z_{body}$ is bio-electrical impedance.

In an example embodiment, variable G may take values, e.g. 0 for female and 1 for male, or other values. In an example embodiment, expression (1), depending on the user's gender, can take the form:

$$TFA = \alpha 0 \cdot BII + \beta 0 \cdot W + \delta 0 \cdot E \text{–for female,}$$

$$TFA = \alpha 1 \cdot BII + \beta 1 \cdot W + \delta 1 \cdot E \text{–for male.}$$

Anthropometric data can be pre-stored in memory and retrieved at step S3 from memory and transferred to the processing unit, or can be entered at step S3 into the processing unit via I/O interface.

Coefficients α, β, γ, δ (or α0, α1, β0, β1, δ0, δ1) may be determined by a neural network trained on the dataset described above (corresponding to a reference sample of people mentioned above), including anthropometric data of users, bio-electrical impedance values and total area of fat (subcutaneous and visceral) in the abdominal region section, determined by a reference method.

In an example embodiment, not all of the above anthropometric data, but only some of them, or various combinations of them, may be used to calculate total fat area. This reduces the computational load and increases the speed of the method.

Based on the conducted studies, it was determined that results of measuring bio-electrical impedance and anthropometric data of the user have a high coefficient of correlation with the total fat area in the abdominal region section.

Figure 4:
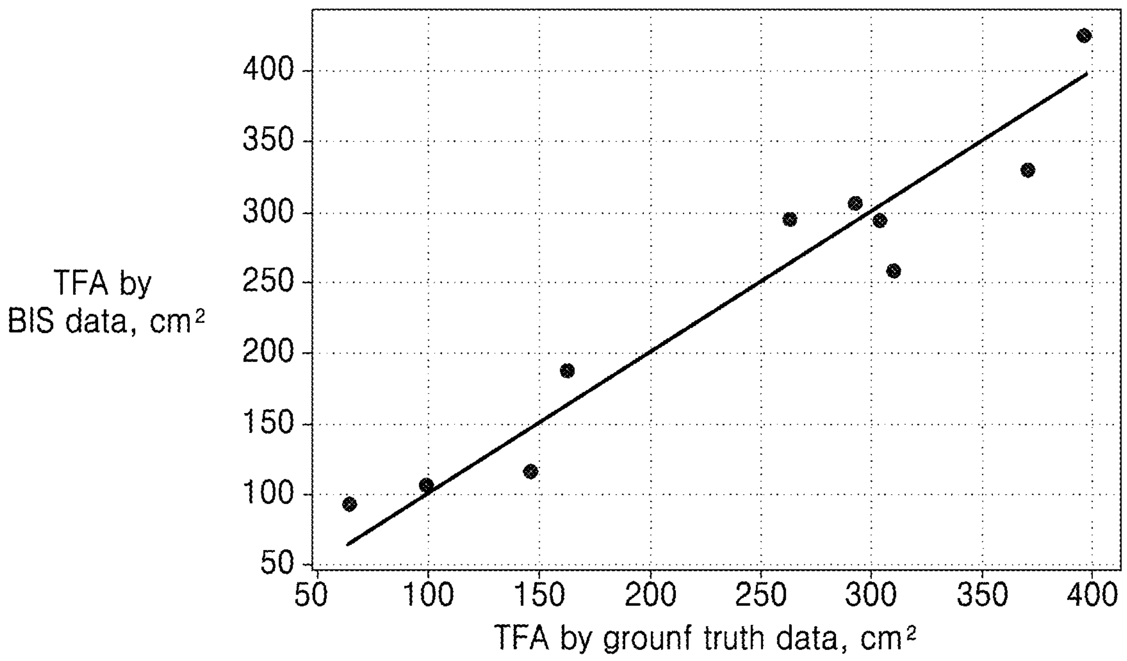
FIG. 4 is a graph illustrating a relationship between total fat area determined by reference method and total fat area calculated according to various embodiments.

FIG. 4 is a graph illustrating total fat area value calculated according to various embodiments from results of bio-electrical impedance measurements versus total fat area value determined by a reference method.

Referring to FIG. 4, in an example embodiment, the vertical axis value of a point may refer to the calculated total fat area and the horizontal axis value of the point may refer to the total fat area determined according to the ground truth data.

Based on the obtained TFA and ASFA data, at step S5 the abdominal visceral fat area (AVFA) is calculated using the equation:

$$AVFA = \vartheta \cdot TPA - \theta \cdot ASFA, \quad (3)$$

where υ and θ are some coefficients (ideally AVFA=TFA−ASFA).

Coefficients υ and θ may also be determined by a neural network trained on the dataset described above (corresponding to a reference sample of people mentioned above), including the subcutaneous fat area and the total fat area in the abdominal region, obtained in accordance with the present disclosure from the results of measurement of reflected radiation which is emitted from UWB radar, results of measurement of bio-electrical impedance and user's anthropometric data, as well as the abdominal visceral fat area, determined using reference method.

Substituting equation (1) into equation (3), obtain:

$$AVFA = \alpha \cdot BII + \beta \cdot W + \gamma \cdot G + \delta \cdot E - \theta \cdot ASFA. \quad (4)$$

Considering that ASFA can be derived from the radar UWB measurement data, e.g. ASFA=f(UWB), obtain:

$$AVFA = \alpha \cdot B// + \beta \cdot W + \gamma \cdot G + \delta \cdot E - \theta \cdot f(UWB). \quad (5)$$

Thus, based on one equation from equations (3) to (5) at step S5, the abdominal visceral fat area (AVFA) in body section is obtained.

Based on the conducted studies, it was determined that the results of measuring the reflected UWB radar signal, results of measuring bio-electrical impedance and anthropometric data have a high coefficient of correlation with the abdominal visceral fat area.

Figure 5:
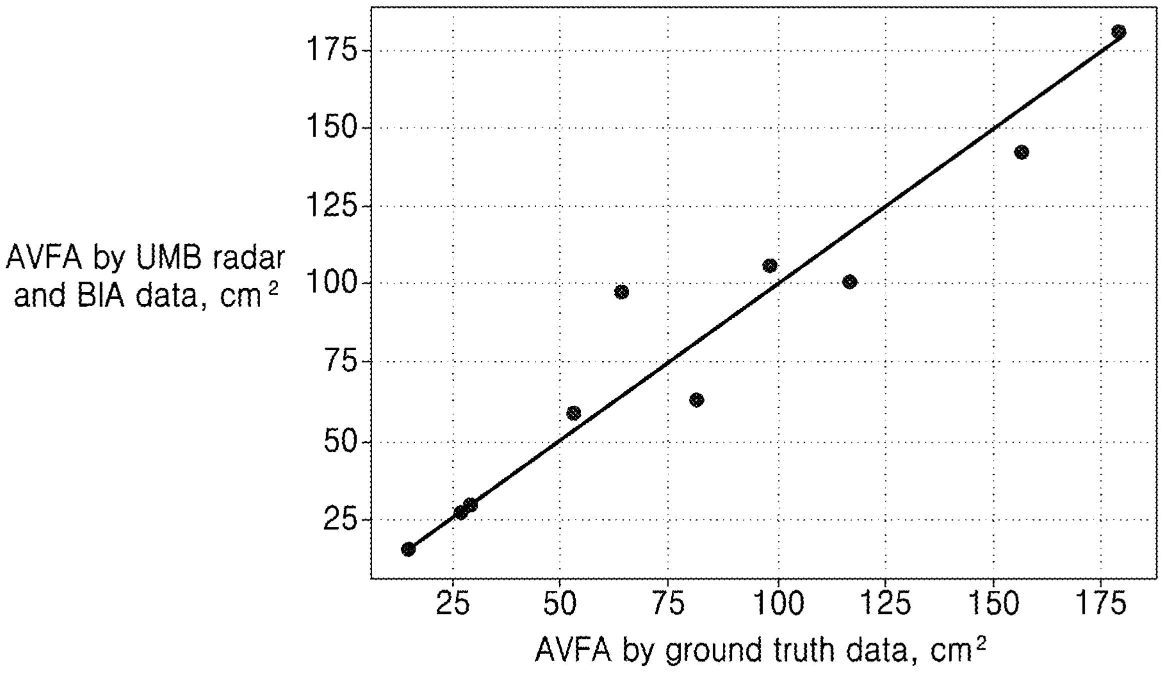
FIG. 5 is a graph illustrating a relationship between visceral fat area determined by reference method and visceral fat area calculated according to various embodiments.

FIG. 5 is a graph illustrating total fat area value calculated according to various embodiments from results of bio-electrical impedance measurements versus total fat area value determined by a reference method.

Referring to FIG. 5, in an example embodiment, the vertical axis value of a point may refer to the calculated abdominal visceral fat area and the horizontal axis value of the point may refer to the abdominal visceral fat area determined according to the ground truth data.

From the above description of the method for determining the abdominal subcutaneous fat area and the abdominal visceral fat area, it can be seen that sequence of method steps is not necessarily the same as previously disclosed. It is apparent that steps S1-S2 and S3-S4 can be performed both simultaneously and sequentially in any order.

In accordance with another aspect of the disclosure, there is provided a system for determining the abdominal subcutaneous fat area and the abdominal visceral fat area, which implements the method described above. The system comprises a ultra-wideband radar device (e.g, including UWB circuitry), a bio-electrical impedance analysis device (e.g., including various circuitry) and a processing unit (e.g., including at least one processor, comprising processing circuitry), wherein the ultra-wideband (UWB) radar device is configured to emit radiation into human body and measure reflected radiation parameters, a bio-electrical impedance analysis device is configured to measure bio-electrical impedance of the body, and at least one processor, individually and/or collectively, is configured to determine the abdominal subcutaneous fat area in the body section from the measurement data obtained by the UWB radar, determine the total fat area in the abdominal region section from the bio-electrical impedance data of the body and the anthropometric data, and calculate the abdominal visceral fat area from the obtained total fat area and the abdominal subcutaneous fat area. The processing unit may include various processing circuitry and/or multiple processors. For example, as used herein, including the claims, the term "processor" may include various processing circuitry, including at least one processor, wherein one or more of at least one processor, individually and/or collectively in a distributed manner, may be configured to perform various functions described herein. As used herein, when "a processor", "at least one processor", and "one or more processors" are described as being configured to perform numerous functions, these terms cover situations, for example and without limitation, in which one processor performs some of recited functions and another processor(s) performs other of recited functions, and also situations in which a single processor may perform all recited functions. Additionally, the at least one processor may include a combination of processors performing various of the recited/disclosed functions, e.g., in a distributed manner. At least one processor may execute program instructions to achieve or perform various functions.

According to an example embodiment, the device with UWB radar may include a smartphone with embedded ultra-wideband radar, and the bio-electrical impedance analysis device may include a smart watch capable of measuring the user's body bio-electrical impedance. Moreover, the processing unit can be located both in the smartphone and on a remote server.

The user's anthropometric data may be previously stored in memory and retrieved from memory and transferred to the processing unit, or may be entered into the processing unit via an I/O interface.

The ultra-wideband radar device and the bio-electrical impedance analysis device are configured to transmit the obtained measurement results to the processing unit for further processing as described above.

In an example embodiment, the device with UWB radar may, for example, and without limitation, be one of a mobile phone, tablet computer, PERSONAL DIGITAL ASSISTANT (PDA), e-book reader, or any other digital mobile device.

In an example embodiment, the bio-electrical impedance analysis device may include a fitness band or an electronic band.

In an example embodiment, the device with UWB radar and the bio-electrical impedance analysis device may be implemented in a single device, e.g. a smartphone. In such an embodiment, the processing unit may also reside in the smartphone. This greatly simplifies both the hardware of the system for determining the abdominal subcutaneous fat area and abdominal visceral fat area, and the process of determining as such.

Thus, various embodiments of the disclosure may provide a simple, accurate, inexpensive and rapid method for estimation of the abdominal subcutaneous fat area (ASFA) and abdominal visceral fat area (AVFA). The method can be performed using personal portable devices without requiring professional stationary medical equipment. UWB radar used in the present disclosure may be a commercially available device that comply with all standard restrictions regarding power and radiation density to ensure safety for the user.

The above example advantages allow the user to independently and at the desired frequency (for example, every day) estimate the abdominal subcutaneous fat area (ASFA) and the abdominal visceral fat area (AVFA), monitor the dynamics of their change and adjust user's diet/treatment/exercise.

One skilled in the art will appreciate that not all of the above advantages are necessarily inherent in each individual embodiment, e.g. different embodiments may have a different set of these advantages and to varying degrees.

In an example embodiment, a system configured to determine abdominal subcutaneous fat area and abdominal visceral fat area comprises: a processing unit including at least one processor, comprising processing circuitry, individually and/or collectively, configured to: recall and execute computer programs from memory for performing method steps or functions of system units in accordance with embodiments of the present disclosure. According to various embodiments, the system may further comprise a memory. The processor may recall and execute computer programs from memory to perform the described method. The memory may be a separate device independent of the processor or may be integrated with the processor.

At least one of the method steps or the system units may use an artificial intelligence (AI) model to perform respective operations. The function associated with AI may be performed through non-volatile memory, volatile memory and the processor.

The processor may comprise one or more processors. Moreover, one or more processors may be a general purpose processor, such as a central processing unit (CPU), an application processor (AP) or the like, a graphics-only processing unit (GPU), a visual processing unit (VPU) and/or an AI-dedicated processor such as a neural processing unit (NPU). The processor may include various processing circuitry and/or multiple processors. For example, as used herein, including the claims, the term "processor" may include various processing circuitry, including at least one processor, wherein one or more of at least one processor, individually and/or collectively in a distributed manner, may be configured to perform various functions described herein. As used herein, when "a processor", "at least one processor", and "one or more processors" are described as being configured to perform numerous functions, these terms cover situations, for example and without limitation, in which one processor performs some of recited functions and another processor(s) performs other of recited functions, and also situations in which a single processor may perform all recited functions. Additionally, the at least one processor may include a combination of processors performing various of the recited/disclosed functions, e.g., in a distributed manner. At least one processor may execute program instructions to achieve or perform various functions.

The one or more processors control the processing of input data in accordance with a predefined operating rule or artificial intelligence (AI) model stored in the non-volatile memory and the volatile memory. The predefined operating rule or artificial intelligence model can be provided through training. In doing so, the processor may perform a pre-processing operation on the data to convert it into a form suitable for use as input to the artificial intelligence model.

Being "provided through learning" may refer, for example to, by applying a learning algorithm to a plurality of learning data, a predefined operating rule or AI model of a desired characteristic being made. The learning may be performed in a device itself in which AI according to an embodiment is performed, and/or may be implemented through a separate server/system.

The artificial intelligence model may include a plurality of neural network layers. Each layer has a plurality of weight values, and performs a layer operation through calculation of a previous layer and an operation of a plurality of weights. Examples of neural networks include, but are not limited to, convolutional neural network (CNN), deep neural network (DNN), recurrent neural network (RNN), restricted Boltzmann Machine (RBM), deep belief network (DBN), bidirectional recurrent deep neural network (BRDNN), generative adversarial networks (GAN), and deep Q-networks The learning algorithm is a method for training a predetermined target device (for example, a GPU-based neural network) using a plurality of learning data to cause, allow, or control the target device to make a determination or prediction. Examples of learning algorithms include, but are not limited to, supervised learning, unsupervised learning, semi-supervised learning, or reinforcement learning.

Various illustrative units and modules described in connection with the disclosure herein may be implemented or executed by a general purpose processor, a digital signal processor (DSP), an application specific integrated circuit (ASIC), a field programmable gate array (FPGA), or other programmable logic device (PLD), discrete logic gate or transistor logic gate, discrete hardware components, or any combination of the foregoing designed to perform the functions described in this disclosure. The general purpose processor may be a microprocessor, but in an example embodiment, the processor may be any conventional processor, controller, microcontroller, or finite state machine. The processor may also be implemented as a combination of computing devices (e.g. a combination of a DSP and a microprocessor, multiple microprocessors, one or more microprocessors together with the DSP core or any other similar configuration).

The memory may be volatile or non-volatile memory, or may include both volatile and non-volatile memory. The non-volatile memory can be Read Only Memory (ROM), Programmable Read Only Memory (PROM), Erasable Programmable Read Only Memory (EPROM), Electronically Erasable Programmable Read Only Memory (EEPROM), or flash memory. The volatile memory can be Random Access Memory (RAM). Also, the memory in embodiments of the present disclosure may be Static Random Access Memory (SRAM), Dynamic Random Access Memory (DRAM), Synchronous Dynamic Random Access Memory (synchronous DRAM, SDRAM), Synchronous Dynamic Random Access Memory With Double Transfer Rate (Double Data Rate SDRAM, DDR SDRAM), Faster Speed Synchronous Dynamic Random Access Memory (Enhanced SDRAM, ESDRAM), Synchronous Link DRAM (SLDRAM) and Direct Access Bus Memory (DR RAM), etc. Therefore, the memory in embodiments of the present disclosure includes, but is not limited to, these and any other suitable types of memory.

The information and signals described herein may be represented using any of a variety of technologies. For example, the data, instructions, commands, information, signals, bits, symbols, and elementary signals that may be illustrated in the above description may be represented by voltages, currents, electromagnetic waves, magnetic fields or particles, optical fields or particles, or any combinations of the above.

The functions described herein may be implemented in hardware, software running on the processor, firmware, or any combination of the foregoing. When implemented in software executed by the processor, the functions may be stored or transferred as one or more instructions or code on a computer-readable medium. Other examples and implementations are within the scope of the disclosure of the present disclosure. For example, due to the software nature the aforementioned functions may be implemented using software running on the processor, hardware, firmware, fixed block, or combinations of any of the above. Features that implement the functions can also be physically located in different positions, including the distribution at which parts of functions are implemented in different physical locations.

Computer-readable media include both non-transitory computer storage media and communication media, including any medium that facilitates transfer of a computer program from one place to another. The non-transitory storage media can be any available media that can be accessed by a general purpose or special purpose computer. By way of example, and not limitation, the non-transitory computer readable media may include Random Access Memory (RAM), Read Only Memory (ROM), Electrically Erasable Programmable Read Only Memory (EEPROM), flash memory, compact disc ROM (CD) or other optical disk storage device, magnetic disk storage device, or other magnetic storage devices, or any other non-durable medium that can be used to carry or store the required program code means in the form of instructions or data structures, and which can be accessed by a general purpose or special purpose computer, or a general purpose or special purpose processor.

It should be understood that this disclosure provides an example principle of operation and basic examples of a method and system for determining the abdominal subcutaneous fat area and abdominal the visceral fat area. Using these principles, one skilled in the art will be able to provide an embodiment of the disclosure without creative effort.

Functionality of an element mentioned in the description or claims as a single element can be practiced by means of several components of the device, and vice versa, functionality of elements mentioned in the description or claims as several separate elements can be practiced by a single component.

In an embodiment, the elements/units of the present system reside in a common housing, can be placed on the same frame/structure/printed circuit board and are structurally connected to each other through assembly operations and operationally connected through communication links. The communication links or channels, unless otherwise indicated, are standard communication links known to specialists, which can be physically implemented without creative efforts. The communication link may be a wire, a set of wires, a bus, a track, a wireless link (inductive, RF, infrared, ultrasonic, etc.). Communication protocols over communication links are known to those skilled in the art and are not disclosed separately.

Operational connection of elements should be understood as a connection that ensures correct interaction of these elements with each other and implementation of one or another functionality of the elements. Particular examples of operational connection may be connection adapted to exchange information, connection adapted to transmit electric current, connection adapted to transmit mechanical motion, connection adapted to transmit light, sound, electromagnetic or mechanical vibrations, etc. The specific type of operational connection is determined by the nature of the interaction of the elements, and, unless otherwise indicated, is provided by known means, using known principles.

The electrical connection of one element/circuit/port/output to another element/circuit/port/output implies that these elements/circuits/ports/outputs can be either directly connected to each other or indirectly through other elements or circuits.

Structural design of elements of the present system is known to those skilled in the art and is not described separately in this disclosure, unless otherwise indicated. Elements of the system can be made from any suitable material. These components can be manufactured using known methods including, by way of example only, machining, investment casting, crystal growth. Assembly, connection and other operations as described herein are also within the knowledge of a person skilled in the art and thus are not be explained in more detail here.

While various example embodiments have been illustrated and described in detail with reference to the accompanying drawings, it should be understood that such embodiments are illustrative only and are not intended to limit the present disclosure, and that the present disclosure should not be limited to the specific arrangements and structures shown and described, since various other modifications and embodiments of the disclosure may be apparent to one skilled in the art based on the information set forth in the description and knowledge of the prior art, without going beyond the idea and scope of this disclosure, including the appended claims and their equivalents. It will also be understood that any of the embodiment(s) described herein may be used in conjunction with any other embodiment(s) described herein.

What is claimed is:

1. A method for determining an abdominal visceral fat area (AVFA) and an abdominal subcutaneous fat area (ASFA) in an abdominal region of a body, comprising:

using a portable smartphone device with ultra-wide band (UWB) radar, emitting radiation into the abdominal region and measuring parameters of reflected radiation at a measurement point;

based on the measured parameters of the reflected radiation obtained by the UWB radar, determining the ASFA in the abdominal region corresponding to the measurement point;

using the portable smartphone and/or a smart watch to acquire anthropometric data and bio-electrical impedance data of the abdominal region;

based on the bio-electrical impedance data of the abdominal region and the anthropometric data, determining total fat area (TFA) in the abdominal region; and calculating the AVFA in the abdominal region by subtracting the ASFA from the determined TFA, wherein determining the ASFA comprises;

comparing the measured parameters of the reflected radiation with specified threshold values corresponding to a specified thickness of abdominal subcutaneous fat, and based on the comparison, obtaining data on the thickness of the abdominal subcutaneous fat at the measurement point and data on the ASFA in the abdominal region corresponding to the measurement point.

2. The method of claim 1, wherein the specified threshold values are determined based on a plurality of measurements taken on a reference sample of people, wherein to match the specified threshold values, the thickness of the abdominal subcutaneous fat and the ASFA are determined by a reference method.

3. The method according to claim 2, wherein the reference method is selected from magnetic resonance imaging and computer-assisted tomography.

4. The method of claim 1, further comprising: determining a specified threshold value to which each of the measured parameters of the reflected radiation is closer among the specified threshold values, and determining a respective thickness value of the abdominal subcutaneous fat.

5. The method of claim 4, wherein based on multiple measurements, the thickness value of the abdominal subcutaneous fat is determined by averaging all obtained thickness values of the abdominal subcutaneous fat based on the measured parameters of the reflected radiation.

6. The method of claim 4, wherein based on multiple measurements, the thickness value of the abdominal subcutaneous fat is determined by determining the thickness value of the abdominal subcutaneous fat occurring more often than other values based on the measured parameters of the reflected radiation, and discarding the other values.

7. The method of claim 1, wherein the measured parameters of reflected radiation include amplitude and/or phase of a signal.

8. The method of claim 1, wherein the measured parameters of the reflected radiation are processed by a neural network trained on a dataset corresponding to a reference sample of people and including values of the thickness of the abdominal subcutaneous fat and ASFA, obtained using a reference method and respective values of the measured parameters of reflected radiation.

9. The method of claim 1, wherein the TFA in the abdominal region in the abdominal region is determined by the equation:

$$TFA = \alpha \cdot BII + \beta \cdot W + \gamma \cdot G + \delta \cdot E,$$

where, BII is a body impedance index of the body, W is a weight, G is a gender, E is an age, α, β, γ, δ are coefficients, wherein:

$$BII = H^2 / Z_{body},$$

where H is a height, and $Z_{body}$ is the bio-electrical impedance value.

10. The method of claim 1, wherein the AVFA is determined by the equation:

$$AVFA = \vartheta \cdot TFA - \theta \cdot ASFA,$$

where υ and θ are coefficients determined by a neural network trained on a dataset corresponding to a reference sample of people and including the ASFA and the TFA in the abdominal region, obtained from the measured parameters of the reflected radiation, the bio-electrical impedance data and the anthropometric data, and the AVFA, determined by a reference method.

11. A non-transitory computer-readable medium that stores instructions causing at least one processor comprising processing circuitry, individually and/or collectively to perform operations of the method of claim 1 when executed.

12. A system configured to determine an abdominal subcutaneous fat area (ASFA) and an abdominal visceral fat area (AVFA), comprising:

a portable smartphone comprising ultra wide-band (UWB) radar circuitry, configured to emit radiation into a body in an abdominal region and measure parameters of reflected radiation at a measurement point;

a bio-electrical impedance analysis device comprising circuitry configured to measure bio-electrical impedance data of the abdominal region, the bio-electrical impedance analysis device comprising the portable smartphone and/or a smart watch; and at least one processor, comprising processing circuitry, individually and/or collectively, configured to:

determine the ASFA in the abdominal region based on the measured parameters of the reflected radiation obtained by the UWB radar;

determine total fat area (TFA) in the abdominal region based on the bio-electrical impedance data of the abdominal region and anthropometric data, and calculate the AVFA in the abdominal region by subtracting the ASFA from the determined TFA, wherein the at least one processor is configured individually and/or collectively, in determining the ASFA, to:

compare the measured parameters of the reflected radiation with predetermined threshold values, corresponding to a specified thickness of abdominal subcutaneous fat, and based on the comparison, obtain data on the thickness of the abdominal subcutaneous fat at the measurement point and data on the ASFA in the body section corresponding to the measurement point.

13. The system of claim 12, wherein the bio-electrical impedance analysis device includes the smart watch capable of measuring bio-electrical impedance of the abdominal region.

14. The system of claim 12, wherein the device including the UWB radar circuitry and the bio-electrical impedance analysis device are implemented in the smartphone.

* * * * *